United States Patent [19]
Lee et al.

[11] Patent Number: 5,951,292
[45] Date of Patent: Sep. 14, 1999

[54] METHOD OF DETECTING PERIODONTAL DISEASE BY DETECTING THE NATURAL FREQUENCY OF A TOOTH.

[76] Inventors: Sheng Yang Lee, 3F., No. 28-1, Lane 97, Sec. 1, Hsin Sheng S. Rd.; Haw Ming Huang, 2F.,-1, No. 186-1, Hsin An St., both of Taipei; Ching Yi Lin, No. 134, Fu Hsing Rd., 14 Hu, Chin Hu Chen, Chin Men Hsien, all of Taiwan

[21] Appl. No.: 09/156,617

[22] Filed: Sep. 18, 1998

[51] Int. Cl.$^6$ ...................................................... A61C 5/00

[52] U.S. Cl. ........................... 433/215; 433/72; 600/589; 600/590

[58] Field of Search ................................ 433/72, 75, 215, 433/629; 33/513, 514; 600/589, 590

[56] References Cited

U.S. PATENT DOCUMENTS

| | | | |
|---|---|---|---|
| 4,482,324 | 11/1984 | Wohlgemuth | 433/72 X |
| 4,881,552 | 11/1989 | Heyman | 433/72 X |
| 5,680,874 | 10/1997 | Takuno | 400/589 X |
| 5,755,571 | 5/1998 | Companion | 433/72 |

*Primary Examiner*—Nicholas D. Lucchesi
*Attorney, Agent, or Firm*—Bacon & Thomas

[57] ABSTRACT

A method of detecting periodontal disease involves attaching a vibration detector to the tooth, causing the tooth to vibrate by means of striking the tooth with a hammer, and then picking up signals corresponding to of the vibration of the tooth for processing by a dynamic signal analyzer and a microprocessor using Fourier analysis. The location of the natural frequency of the tooth is determined based on the lowest point in the image mode and the point of contraflexure in the real mode.

7 Claims, 4 Drawing Sheets

METHOD OF DETECTING PERIODONTAL DISEASE BY DETECTING THE NATURAL FREQUENCY OF A TOOTH.

BACKGROUND OF THE INVENTION

The invention provides a method of detecting of a periodontal disease through determination of the natural frequency of a tooth.

When inspecting for periodontal disease, a dentist usually measures the depth of the periodontal pocket or the height of the surrounding area of the tooth in question. It is important to obtain the relevant data accurately. A probe is mostly commonly used for inspecting for periodontal disease. However, it is inconvenient to operate a probe in inspecting for periodontal disease, and likewise inconvenient to check the scales of the probe visually. The accuracy of using a probe to inspect for periodontal disease may be affected by various factors including the diameter of the probe used, the positioning of the probe in the periodontal tissues, or the force applied by the dentist. There is another method of inspecting for periodontal disease, referred to as a Periotest. However, a Periotest cannot accurately detect the depth of the periodontal pocket, and the intensity of force applied to the Periotest may affect the result of the inspection. Therefore, this method cannot eliminate human error. X-ray films may also be used for inspecting the depth of the tooth sac. However, an X-ray film cannot show a three-dimensional image. Further, because X-rays maybe harmful to one's health, it is not recommended to receive X-rays for a long term exposure.

SUMMARY OF THE INVENTION

The present invention has been developed in order to eliminate the aforesaid problems. Using this new method, a vibration detector is attached to the tooth. A hammer strikes the tooth, causing vibrations, which are picked up by the vibration detector, then processed through a dynamic signal analyzer and a microprocessor using Fourier analysis. The location of the natural frequency of the tooth can then be determined from the frequency domain using to the lowest point in the image mode and the point of contraflexure in the real mode.

DETAILED DESCRIPTION OF THE PREFERRED EMBODIMENT

Figure 1:
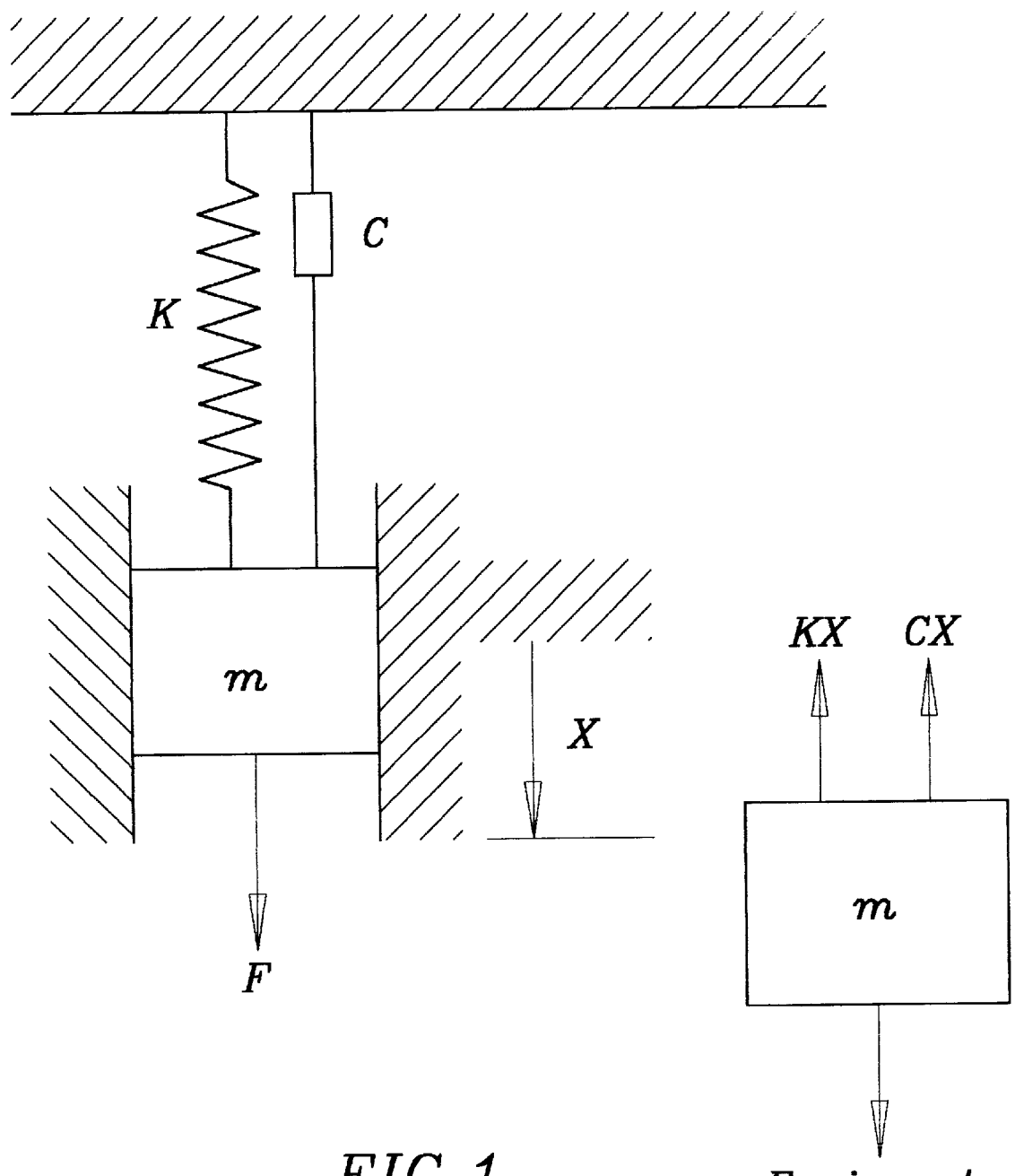
FIG. 1 explains the formation of a natural frequency.

Referring to FIG. 1, the natural frequency defined herein means the frequency which is produced by a object (for example a tooth) when the object is forced to vibrate. According to the laws of dynamics, when a mass point having an elastic power and a mass is acted on by an external sine force, the mass point m is forced to vibrate subject to the follow equation:

$$m\ddot{x} + c\dot{x} + kx = F_0 \sin\omega t$$

When $x = x\sin(\omega t - \phi)$, $$x = \frac{F_0/k}{\sqrt{\left(1 - \frac{m\omega^2}{k}\right)^2 + \left(\frac{c\omega}{k}\right)^2}}$$

in which $\omega$ is added striking frequency. When $$\omega = \sqrt{\frac{k}{m}},$$

x has maximum value and the amount of vibration reaches the extent that the mass system is in a resonant state. In the resonant state the frequency $\omega$ is approximately equal to the natural frequency of the mass, which is a function of elasticity k and the mode of the mass m. This explanation is derived from the dynamic balance equation. Therefore, the natural frequency is also called the dynamic parameter of the matter. The energy is directly proportional to the frequency. When its frequency is high, the mass point is not easily vibrated. In actual application, only low levels of natural frequency are observed.

According to the relationship between the periodontal tissues and the teeth, each tooth has one end embedded in the periodontal tissues and the other end suspended in the air, and the vibrating frequency of the teeth can be described by:

$$\omega = \beta_n^2 \sqrt{\frac{EI}{\rho}} = (\beta_n l)^2 \sqrt{\frac{EI}{\rho l^4}}$$

in which $\omega$ is the natural frequency, 1 is the length of the beam, E is Young's module, I is moment of inertia, $\rho$ is the mass of a unit length, and $\beta_n$ is a boundary condition. When a periodontal disease occurs, the boundary condition will be relatively changed, causing the natural frequency of the teeth to be proportionately changed. Therefore, the change in the periodontal tissues can be measured through the natural frequency of the teeth.

Figure 2:
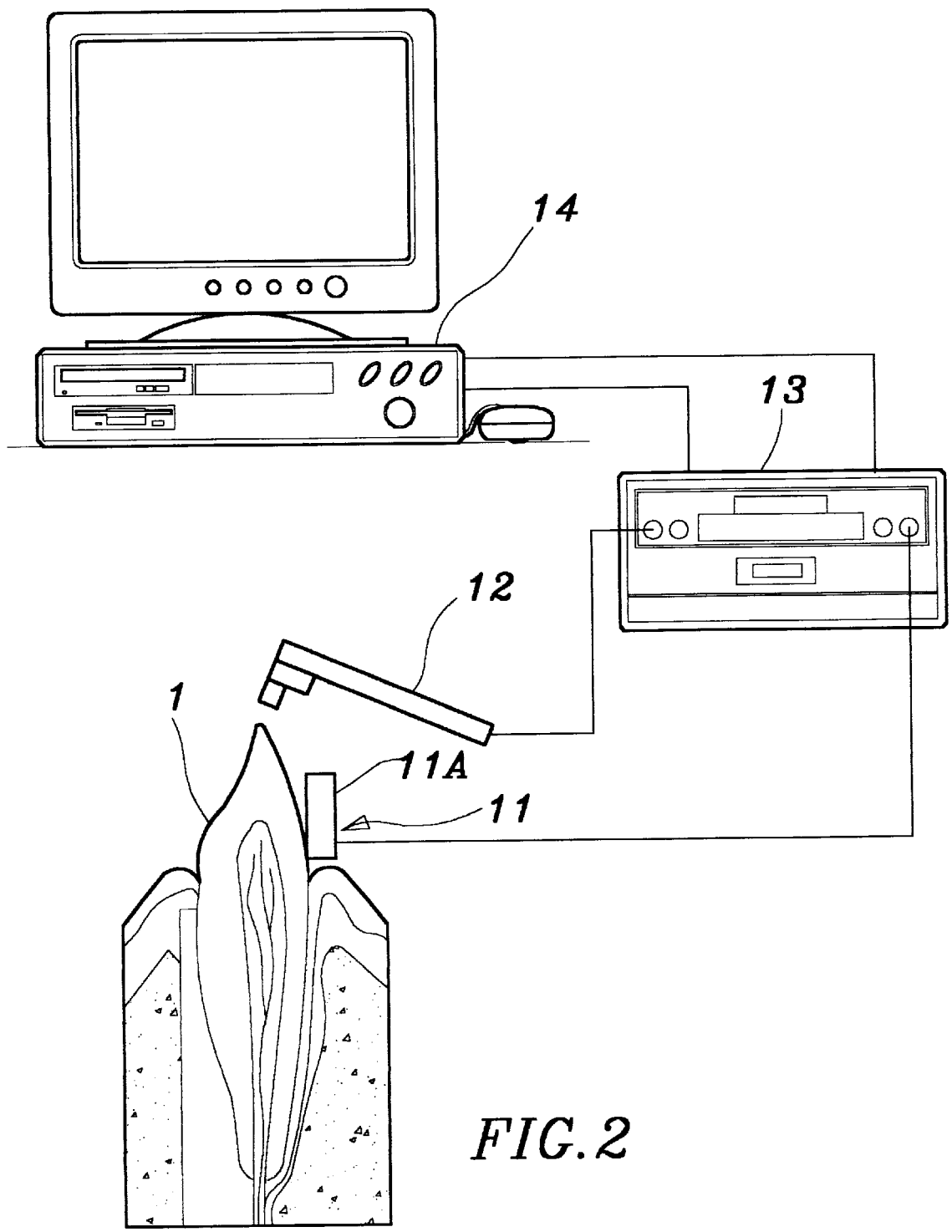
FIG. 2 shows an sample application of the present invention.

Referring to FIG. 2, a vibration detector 11 (for example, acceleration gauge 11A) is closely attached to the tooth 1 adjacent to the gum, and a hammer 12 is used to hit the tooth 1, causing the tooth 1 to vibrate. The vibration of the tooth 1 is detected by the vibration detector 11, causing the vibration detector 11 to output a signal indicative of the vibration of the tooth 1 to a dynamic signal analyzer 13, which is controlled by a microprocessor 14. One signal for every three actions (strikes of the hammer 12) is selected for analysis by means of Fourier's analysis. Thus, the location of the natural frequency of the tooth 1 in the frequency domain is obtained.

Figure 3:
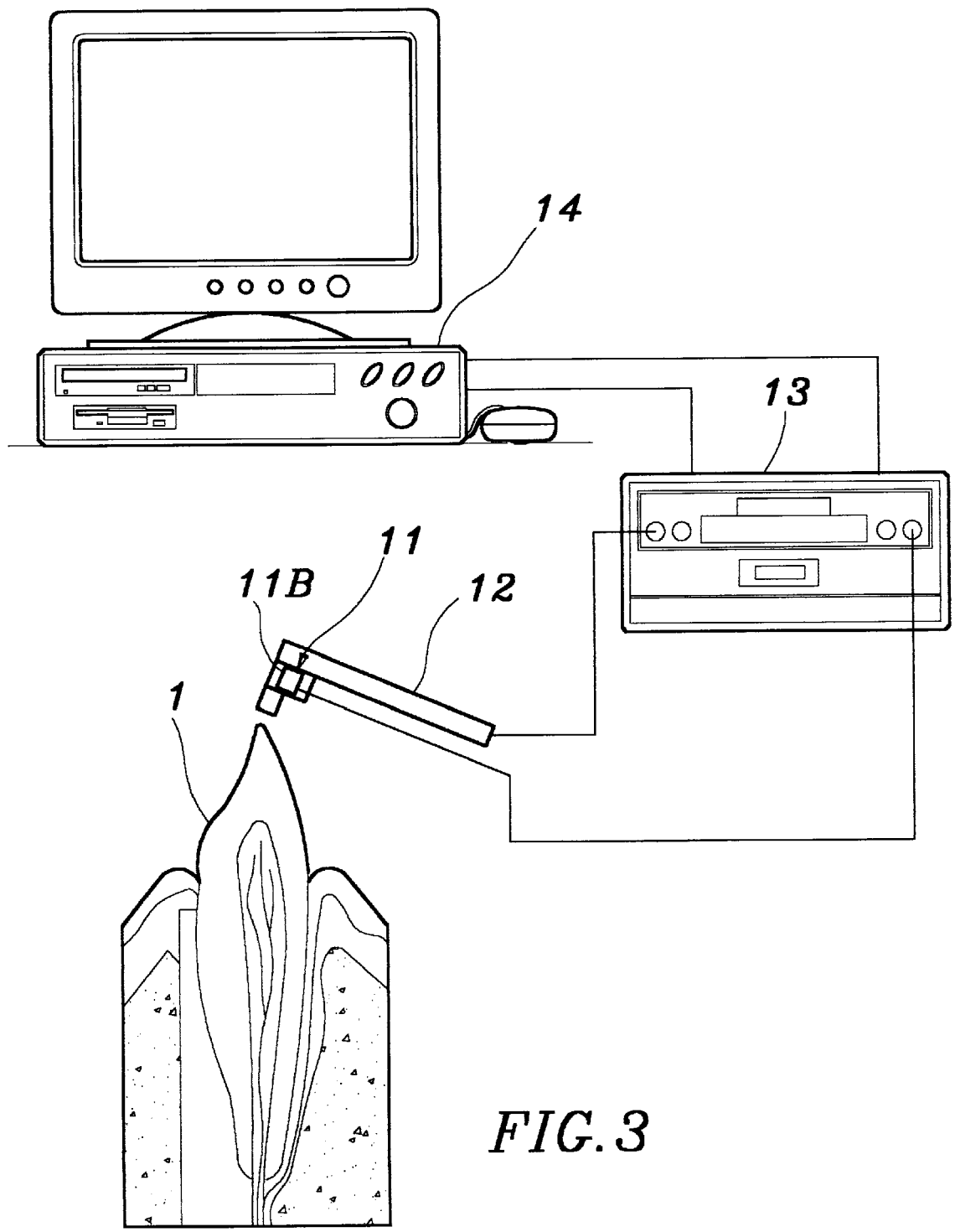
FIG. 3 shows another sample application of the present invention.

Referring to FIG. 3, the oscillation detector 11 can be a microphone 11B mounted on the hammer 12. When the hammer 12 hits the tooth 1, the microphone 11B immediately picks up a vibration signal.

Figure 4:
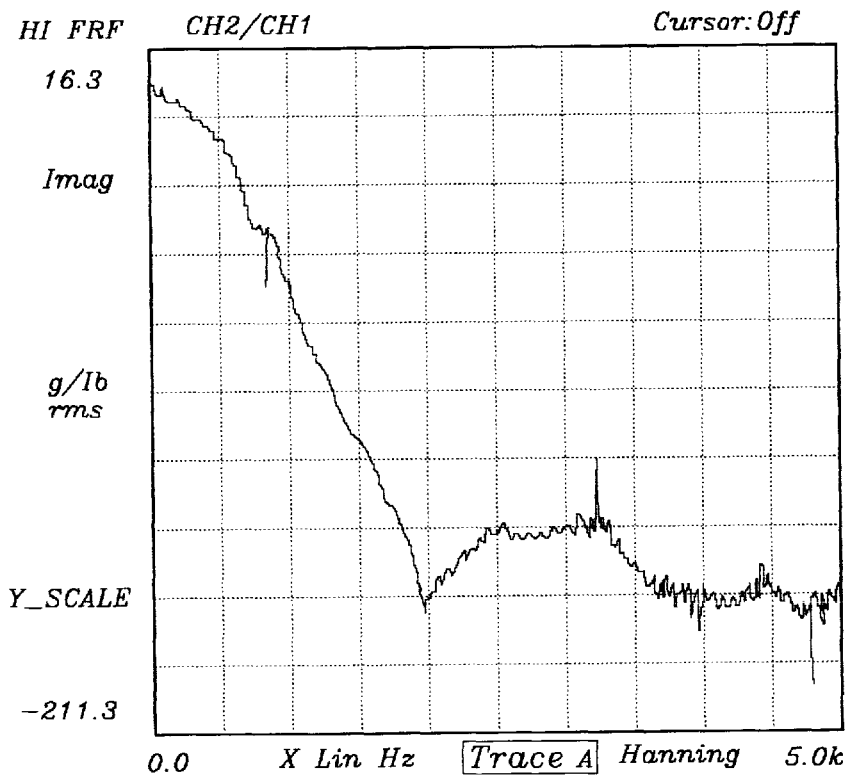
FIG. 4 presents an image mode frequency spectrum.
Figure 5:
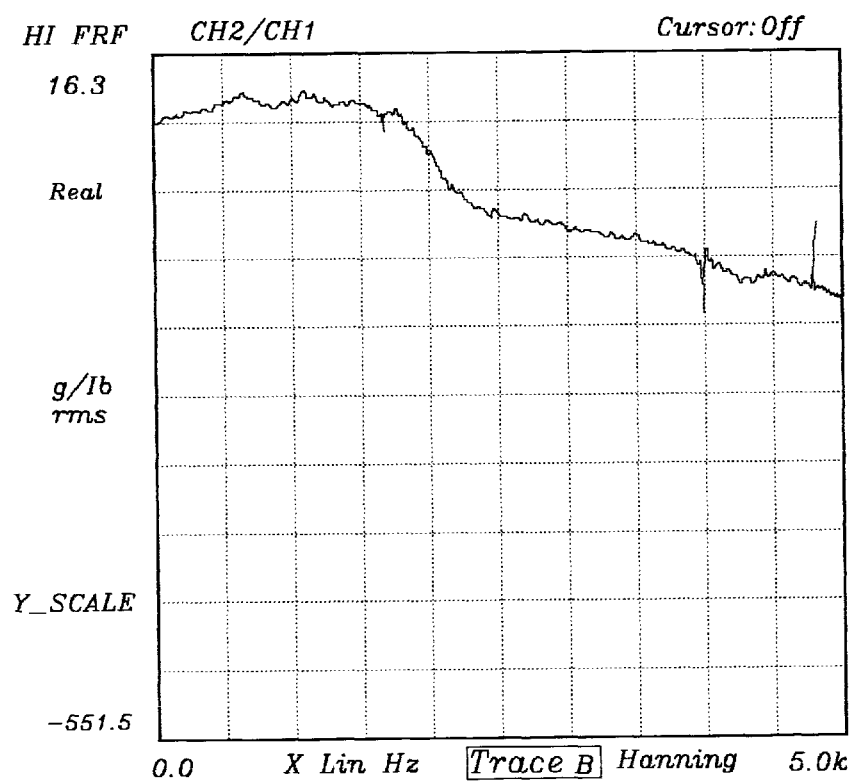
FIG. 5 presents a real mode frequency spectrum.

Referring to FIGS. 4 and 5, the location of the natural frequency is judged by means of the relative lowest point in the Image Mode shown in FIG. 4 and the point of contraflexure in the Real Mode shown in FIG. 5. In FIG. 4, the X-axis is the frequency, and the Y-axis is the image mode. In FIG. 5, the X-axis is the frequency, and the Y-axis is the real mode. The location of the natural frequency is obtained from the relative minimum value in the image mode and the point of contraflexure in the real mode. Because the natural frequency of the tooth induced by means of an impact against the tooth has no relation to the intensity of force applied by the operator, human error is eliminated. And because the method of the present invention is neither intrusive not destructive, it is suitable for use in hospitals as well as at home for long-term tracking of the course of the disease.

It is to be understood that the drawings are designed for purposes of illustration only, and are not intended as a definition of the limits and scope of the invention disclosed.

What the invention claimed is:

1. A method of detecting periodontal disease, comprising the steps of:

vibrating a tooth by striking the tooth with an object and detecting vibrations of the tooth induced by impact of the object with the tooth;

performing a frequency domain analysis of a signal indicative of said vibrations in order to locate a natural frequency of the tooth, the natural frequency of the tooth depending on the health of the gums supporting the tooth.

2. A method as claimed in claim 1, wherein the natural frequency of the tooth is located at a lowest point in an image mode analysis of the frequencies.

3. A method as claimed in claim 1, wherein the natural frequency of the tooth is located by a real mode analysis of a point of contraflexure.

4. A method as claimed in claim 1, wherein the signal indicative of the vibrations is obtained by attaching a vibration detector to the tooth and then hitting the tooth with a hammer.

5. A method as claimed in claim 1, wherein the step of analyzing the signal indicative of the vibrations of the tooth is carried out by supplying the signal to a dynamic signal analyzer in order to perform a Fourier transform of the signal, and supplying the resulting Fourier-transformed signal to a microprocessor for analysis.

6. A method as claimed in claim 1, wherein the step of detecting said vibrations is carried out by an acceleration gauge.

7. A method as claimed in claim 1, wherein the step of detecting said vibrations is carried out by a microphone.

* * * * *